United States Patent
Chiang et al.

(10) Patent No.: US 10,978,209 B2
(45) Date of Patent: Apr. 13, 2021

(54) METHOD OF AN INTERACTIVE HEALTH STATUS ASSESSMENT AND SYSTEM THEREOF

(71) Applicant: NATIONAL CHENG KUNG UNIVERSITY, Tainan (TW)

(72) Inventors: Jung-Hsien Chiang, Taichung (TW); Pei-Ching Yang, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 162 days.

(21) Appl. No.: 16/206,801

(22) Filed: Nov. 30, 2018

(65) Prior Publication Data
US 2020/0176116 A1 Jun. 4, 2020

(51) Int. Cl.
*G16H 50/30* (2018.01)
*G10L 15/26* (2006.01)
(Continued)

(52) U.S. Cl.
CPC ........ *G16H 50/30* (2018.01); *G06F 16/90332* (2019.01); *G10L 15/26* (2013.01); *H04L 51/02* (2013.01)

(58) Field of Classification Search
CPC ........ G16H 50/30; G16H 10/20; G16H 80/00; G16H 40/20; G16H 50/00; G16H 10/60; G16H 50/70; G16H 15/00; G10L 15/26; G10L 17/00; G06F 16/90332; G06F 40/35; G06F 40/279; G06F 40/30; G06F 40/20; G06F 40/117; G06F 16/93;
(Continued)

(56) References Cited

U.S. PATENT DOCUMENTS

| 5,357,427 A * | 10/1994 | Langen | G06F 19/3418 |
| | | | 600/300 |
| 8,630,875 B2 * | 1/2014 | Iliff | G06F 19/30 |
| | | | 705/3 |

(Continued)

OTHER PUBLICATIONS

International Search Report in application No. PCT/US2018/063478 dated Feb. 26, 2019.
(Continued)

*Primary Examiner* — Eliza A Lam
(74) *Attorney, Agent, or Firm* — Maschoff Brennan

(57) ABSTRACT

A system of interactive health status assessment comprises a dialogue database including a plurality of health status assessment questions presented by a data output interface; a multimodal data input interface is configured to receive a response information; an identification module is configured to determine the type of the response information; a semantic interpretation module is configured to extract a keyword from the text-type response information; a health status assessment module is configured to generate a first assessment result according to the numeric-type response information, a second assessment result is generated according to the keyword, and an outputted assessment report is generated according to the assessment results; and a control module is configured to selectively notify the health status assessment module to output the assessment report or select another health status assessment question from a follow-up item of the selected health status assessment question.

9 Claims, 3 Drawing Sheets

(51) Int. Cl.
  *H04L 12/58*   (2006.01)
  *G06F 16/332*  (2019.01)
  *G06F 16/9032* (2019.01)

(58) Field of Classification Search
  CPC ........... G06F 16/9535; G06F 16/24578; G06F 19/325; G06F 19/328; H04L 51/02; G06Q 30/0233; G06Q 20/29
  See application file for complete search history.

(56) References Cited

U.S. PATENT DOCUMENTS

| | | | |
|---|---|---|---|
| 9,553,727 B2* | 1/2017 | Kia | ............... H04L 63/0861 |
| 2012/0191466 A1 | 7/2012 | Quint et al. | |
| 2014/0114680 A1 | 4/2014 | Mills et al. | |
| 2017/0262609 A1* | 9/2017 | Perlroth | ............... G16H 50/30 |
| 2018/0070873 A1* | 3/2018 | Cronin | ............... G16H 50/30 |

OTHER PUBLICATIONS

Hung et al., "Predicting Negative Emotions Based on Mobile Phone Usage Patterns: An Exploratory Study", JMIR Research Protocols, vol. 5, Iss. 3, Jul. 2016.

Hung et al., "Capturing Depression with Your Smartphone Validity and Utilization of iHOPE for Depressed Patients in Taiwan", 24th European Congress of Psychiatry, Mar. 2016.

Yang et al., "Literature-based discovery of new candidates for drug repurposing", Briefings in Bioinformatics, 18(3), May 2017.

Kim et al., "Cancer stem cell molecular markers verified in vivio", Biochemistry (Moscow) Supplement Series B Biomedical Chemistry, Jan. 2017.

Chang et al., "Using Heterogeneous Social Media as Auxiliary Information to Improve Hotel Recommendation Performance", IEEE, vol. 6, Jul. 2018.

Yang et al., "Gene ontology concept recognition using named concept: understanding the various presentations of the gene functions in biomedical literature", Database, Oct. 2018.

Wang et al., "Detecting Potential Adverse Drug Reactions Using a Deep Neural Network Model", Journal of Medical Internet Research, vol. 21, Iss. 2, Feb. 2019.

Hao et al., "Real-time event embedding for POI recommendation", Neurocomputing 349, Apr. 2019.

International Search Report dated Feb. 26, 2019 as received in Application No. PCT/US2018/063478.

Written Opinion of the International Searching Authority dated Feb. 26, 2019 as recived in Application No. PCT/US2018/063478.

* cited by examiner

METHOD OF AN INTERACTIVE HEALTH STATUS ASSESSMENT AND SYSTEM THEREOF

FIELD OF THE DISCLOSURE

The present disclosure relates to health status assessment, and more particularly to an interactive health status assessment system and method thereof.

BACKGROUND

The arrival of an aging society has made the long-term care of the elderly people one of the most concerned issues in modern society and families. On the other hand, under the rapid development of interaction between robots and artificial intelligence, the homecare services that can be provided are more and more diversified. For example, robots with health care and companionship function can help people to care for elders at home or elders living alone. Technologize care work can ease the pressure of the shortage of long-term care givers. In medical care situations, robots can assist healthcare professionals in repetitive health education, allowing medical staff to focus on individual care needed for patients to improve medical quality.

However, existing systems that combine artificial intelligence technology and health care lack an interactive mechanism with the object being cared for. We communicate using words, a form of unstructured data. If the software of above system lacks the design of deep semantic understanding, it can only rely on experiences on similar things or similar users to assist in judging. Thus, said system usually fails to provide smarter health status assessment results based on current user preferences, causality and context, and is often difficult to accurately detect the user's intention when interacting with the user.

SUMMARY

In view of this, the present disclosure proposes an interactive health status assessment system and an interactive health status assessment method to solve the above problems.

An interactive health status assessment method according to an embodiment of the present disclosure includes: selecting a health status assessment question from a dialog design database and presenting the health status assessment question by using a data output interface, wherein the dialog design database includes a plurality of health status assessment questions, each health status assessment question has a follow-up item, and the follow-up item corresponds to zero or at least another health status assessment question in the dialog design database; after the question of the health status assessment is presented in the data output interface, the multimodal data input interface receives the reply information; the identification procedure determines the type of the reply information; when the reply information belongs to the numerical type, the health status assessment program generates the first evaluation result and stores the first evaluation result according to the reply information and the numerical rule in the temporary storage space; when the reply information belongs to the text type, the semantic understanding program extracts the keyword from the reply information, and the health status evaluation program generates the second evaluation result according to the keyword and stores the second evaluation result in the temporary storage space; after the result is generated in the first evaluation result or the second, judging whether the interactive end signal is received; when the interactive end signal has been received, the health status evaluation program outputs an evaluation report according to the data in the temporary storage space; when the interactive end signal is not received, select another health status assessment question in the follow-up item.

An interactive health status assessment system according to an embodiment of the present disclosure includes: a dialog design database, including a plurality of health status assessment questions, each health status assessment question has a follow-up item, and the follow-up item corresponds to zero or at least one other health status assessment question in the dialog design database; a data output interface for health status assessment, communicatively connected to the dialog design database; multimodal data input interface for receiving responses information; an identification module communicatively connected to the multimodal data input interface, wherein the identification module is used to judge whether the response information belongs to text type or numerical type; a semantic interpretation module, communicatively connected to the identification module, for categorizing the information type by taking a keyword; a health status evaluation module, communicatively connected to the identification module and the semantic interpretation module, and is configured to generate a first evaluation result from the response information and a numerical rule belonging to the numerical type response, and generate a second evaluation according to the keyword, and storing of first and second assessments to a temporary storage space, also outputting an evaluation report according to the data of the temporary storage space; and a control module, communicatively connected to the dialogue design database, a multimodal data input interface, and a health status evaluation module, and the control module is configured to output a health status assessment evaluation report when received the interactive end signal. Also, another health status assessment question is selected from the follow-up item of the health status assessment question when the interactive end signal is not received.

With the above technology, the interactive health status assessment system and method thereof disclosed by the present disclosure can interpret the semantic meaning and better understand the user's intentions and needs through user dialogue.

The above description of the disclosure and the following embodiments are intended to illustrate and explain the spirit and principles of the invention, and to provide further explanation of the scope of the invention.

DETAILED DESCRIPTION

The detailed features and advantages of the present disclosure are described in detail below in the embodiments of the present disclosure. The features and advantages associated with the present disclosure can be readily understood by those skilled in the art. The following examples are intended to describe the present disclosure in further detail, but do not limit the scope of the invention in any way.

The interactive health status assessment system and method thereof disclosed in the present disclosure, in addition to paying particular attention to the interaction between the system and the user, further evaluate the user's health status through the interactive questions and answers designed by the present disclosure. The following is a description of a hardware architecture embodiment of the interactive health status assessment system of the present disclosure as well as the functions of the components in the system. The present disclosure further introduces another hardware architecture embodiment and its applications while introduces an interactive implementation based on the health status assessment method finally.

Figure 1A:
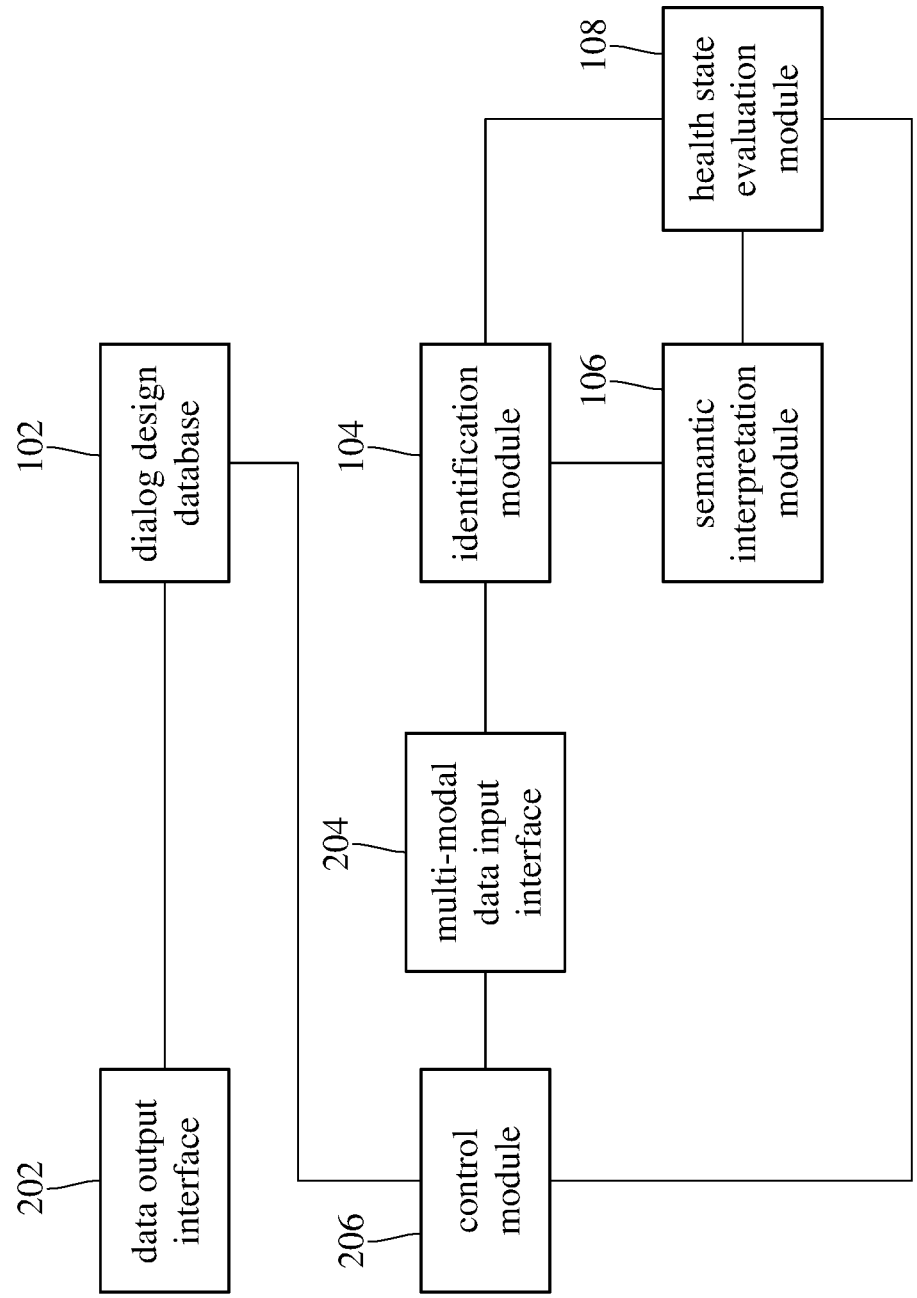
FIG. 1A is a schematic of a block diagram of an interactive health status assessment system according to an embodiment of the present disclosure.

Please refer to FIG. 1A, which illustrates an interactive health status assessment system according to an embodiment of the present disclosure, including: a dialog design database 102, an identification module 104, a semantic interpretation module 106, a health status evaluation module 108, a data output interface 202, a multimodal data input interface 204 and a control module 206. Specifically, the dialog design database 102 may be implemented by a memory device; and the identification module 104, the semantic interpretation module 106, the health status evaluation module 108, and control module 206 may be implemented by individual calculating devices or be integrated into a single calculating device.

The dialog design database 102 stores a plurality of health status assessment questions in a data sheet format. Each health status assessment question has a follow-up item. The follow-up item corresponds to zero or at least one other health status assessment question in the dialog design database 102. In an embodiment, each health status assessment question has a response keyword set corresponding to the follow-up item. In another embodiment, each health status assessment question has a trigger keyword set.

Please refer to Table 1 below, which is an example of a data sheet in the dialog design database 102. In one embodiment, all health status assessment questions in the dialog design database 102 fall in a variety of contents, such as sleep, blood glucose, blood pressure, end-of-answer, and the alike. In the data sheet, each health status assessment question corresponds to a number and a question script. The use of the remaining fields in the data sheet will be described later in relation with the functions of other modules.

TABLE 1

An example of a data sheet for the dialog design database 102.

| Intention | Number | Question script | Trigger keyword set set | Response keyword set set | Answer script | Continual item |
|---|---|---|---|---|---|---|
| Sleep | Q1 | Did you sleep well last night? | N/A | Yes | Sleep good and sleep full is a good method for remaining awaken and energetic | Q7 |
|  |  |  |  | No, Not really, Bad, Very bad, Poor, Very poor |  | Q3 Q5 |
|  | Q3 | Did you drink something containing caffeine before you sleep last night? | Sleep, Not good, Bad, Poor | Yes No | . . . . . . | Q7 Q5 |
|  | Q5 | Did you use cellphone or computer before you sleep last night? | Sleep, Not good, Bad, Poor | Yes No | . . . . . . | Q7 Q7 |
| blood glucose | Q7 | . . . | Palpitations, hand shaking, cold sweat | . . . | . . . | . . . |
|  | Q9 | . . . | . . . | . . . | . . . | . . . |
| . . . Ending | . . . Q99 | . . . Any other questions? | . . . End | . . . Yes | . . . . . . | . . . Q11 Q21 Q31 |
|  |  |  |  | No | . . . | Empty |

Please continue to refer to FIG. 1A. The data output interface 202 electrically connects and communicates with the dialog design database 102, and the data output interface 202 is used to present selected health status assessment questions to the user by visual or audio ways. In practice, the data output interface 202, such as a screen or a speaker, displays text or images, animated characters, or plays a selected health status evaluation question by voice. Although the present disclosure relates shows hardware types of the data output interface 202 and the media of the output questions, they are not thus limited.

After the user obtains a health status assessment question from the data output interface 202, the multimodal data input interface 204 of the interactive health status assessment system according to this embodiment of the present disclosure receives the response information from the user. In practice, the multimodal data input interface 204 can employ hardware devices such as a microphone, a camera, a touch screen, a physiological information measuring instrument (such as a blood glucose meter), or a computer peripheral device; The input modes to the multimodal data input interface 204 are, for example, voice input, image input, click screen input, Bluetooth transmission or wireless transmission; and the data format of the reply information may include sound, image, trigger signal, text and/or number.

Please continue to refer to FIG. 1A. The identification module 104 is communicatively coupled to the multimodal data input interface 204, and the identification module 104 is configured to execute an identification procedure, such as software or code running on the processor. The identification procedure is used to determine whether the reply information belongs to a text type or a numerical type. For example, the voice signal received by the microphone (multimodal data input interface 204) is converted into text, or the electronic signal measured by the blood glucose meter is converted into a numerical value. Specifically, numerical types of data represent can be, for example, vital signs such as the body temperature, blood pressure, heart rate, and respiratory rate, or physiological data such as blood sugar, blood lipids, and the alike.

Please continue to refer to FIG. 1A. The semantic interpretation module 106 electrically connects and communicates with the identification module 104. The semantic interpretation module 106 is used to execute a semantic interpretation program, such as a software or program code running on a processor or a database with a plurality of keywords. The semantic interpretation program is used to retrieve one or several keywords from the response information belonging to the text type. Grammar and semantic analysis are achieved by neural network or machine learning. In other words, the semantic understanding program converts the text into a language framework of ideas, from which the user's intentions and the keywords answered by the user are taken out, for example, understanding that the current user is talking about sleep problems or blood sugar problems.

Please continue to refer to FIG. 1A. The health status evaluation module 108 electrically connects and communicates with the identification module 104 and the semantic interpretation module 106 for performing a health status evaluation program, such as a software or program code running on the processor. The health status assessment program is used to generate a first evaluation result from the response information and a numerical rule correspond to the numerical status. For example, the value measured according to the blood glucose meter is compared with a pre-stored normal range blood glucose value (numerical rule) to generate a first evaluation result. In addition, when the semantic interpretation module 106 retrieves the keywords, the health status assessment module 108 is also operative to generate a second evaluation result based on the keywords and the health status assessment questions selected from the dialog design database 102.

When the multimodal data input interface 204 obtains the information input from the user, the health status evaluation module 108 generates at least one of the first evaluation result and the second evaluation result, and stores the generated evaluation result in one temporary storage space. The user's reply may include only text data or numeric data; however, it is also possible to include both. For example, the user tells the system "I didn't sleep well last night and should have a fever of more than 38 degrees." In this example, the health status assessment module 108 will generate a second evaluation result based on keywords such as "sleep" and "bad", and generate a first evaluation result based on the "38 degrees" of the numerical data. When the interactive health status assessment system according to an embodiment of the present disclosure detects that the user completes the health status assessment process, or detects that the user interrupts the health status assessment process, the health status assessment module 108 will output the evaluation report based on the stored data in the temporary storage space. In another embodiment of the present disclosure, the interactive health status assessment system may further include a user database for storing a historical assessment report for each user. Therefore, whenever the user generates a new evaluation report through the system, the health status evaluation module 108 can further incorporate the historical data into this new evaluation report, thereby more accurately reflecting the health status of the user.

Please continue to refer to FIG. 1A. The control module 206 communicatively connects the dialog design database 102, the multimodal data input interface 204, and the health status evaluation module 108, thereby cooperating with the above components to perform an interactive health status assessment process. In practice, the control module 206 is, for example, a software or program code running on a processor. Upon receiving the interactive completion signal, the control module 206 notifies the health status assessment module 108 to output an evaluation report; when the interaction completion signal is not received, the control module 206 selects another health status assessment question from the follow-up item of the health status assessment question. The interactive completion signal is generated by the multimodal data input interface 204, such as a press toward the return button on the touch screen or a sound of "end interaction" to the microphone, or generated after the system detects the following condition that, for example, the user has responded to a certain number of health status assessment questions in the dialog design database 102 to achieve a certain level of interaction.

The situation in which control module 206 selects another health status assessment question is described below. In another embodiment of the present disclosure, the control module 206 further performs: determining whether the keyword conforms to the response keyword set, and selecting the follow-up item corresponding to the response keyword set when the keyword matches the response keyword set. Please refer to Table 1. For example, when the question currently selected is Q3: "Did you drink something containing caffeine before you sleep last night?", the response key of Q3 contains "Yes" and "No". When the control module 206 confirms that the keyword extracted by the semantic interpretation module 106 contains "Yes", according to the follow-up item field of Q3 in Table 1, Q7 is selected as the next health status assessment question for user to answer. When there are multiple question numbers in the follow-up items, one of them is randomly selected as the next health status assessment question, or the questions are placed in the queue to sequentially query the user.

In another embodiment of the present disclosure, the control module 206 further performs: searching for another health status assessment question from the trigger keyword set which is the same as this health status assessment question. For example, when the current question is Q3, the user does not directly ask questions, but describes that he was "cold sweating" last night. When the control module 206 confirms that the keyword extracted by the semantic interpretation module 106 contains "cold sweat", it searches all the "trigger keyword sets" in Table 1 and finds Q7, so selects Q7 as the next health status assessment question to be asked. In practice, when the user's reply signal includes both "trigger keyword set" and "response keyword set", the next selected health status assessment question can be determined according to the priority of the two, or one of them can be randomly selected to be the first question. The present disclosure is not thus limited.

In practice, in the dialog design database 102, the next question number set in the follow-up item is mostly set to other questions of the same intent category. Therefore, the system can make more comprehensive questions about the same intent category in order to gain a deeper understanding of the user's situation. In still another embodiment of the present disclosure, the control module 206 further calculates a user completion for each intent category. The "user completion" is, for example, a percentage obtained by dividing the number of questions answered by the user by the total number of questions in the category. Therefore, when the system selects the next health status assessment question, if the follow-up item includes several candidate question numbers, the system will first determine whether the user completion degree of the intent category to which the question belongs has reached a preset threshold. If not, the system will select another question from the follow-up item, which belongs to the same intent category as the current question, until the number of questions reaches the preset threshold for the completion degree of the intent category, then the system selects another question of other intent category for the user to continue to answer. Even if the user may first jump to the other intent category through the "trigger keyword set", the system will return to the previous intent category and continue to ask questions after the completion of the intent category being jumped to is reached.

When the follow-up item selected in the dialog design database 102 according to the current health status assessment question is empty (such as Q99), the system will end the interactive questions and answers process. In the foregoing case, for example, after the user completes a certain number of interactive questions and answers, the system determines that sufficient information has been collected, and can generate an evaluation report for the user to review, thus leaves the interactive questions and answers process. Otherwise, for another example, the interactive questions and answers process can stop when the user wants to terminate the interaction. In the questions and answers process, the control module 206 will provide Q99 in the dialog design database 102 to confirm whether the user has other comments to offer. If the user selects "No", the interactive questions and answers process is ended.

According to the above mechanism of selecting the next health status assessment question, the interactive health status assessment system described in one embodiment of the present disclosure can have a closer understanding of the user's semantics, and knowing more about the user's intention and needs. At the same time, according to the response information provided by the user, it provides a more accurate health status assessment.

Figure 1B:
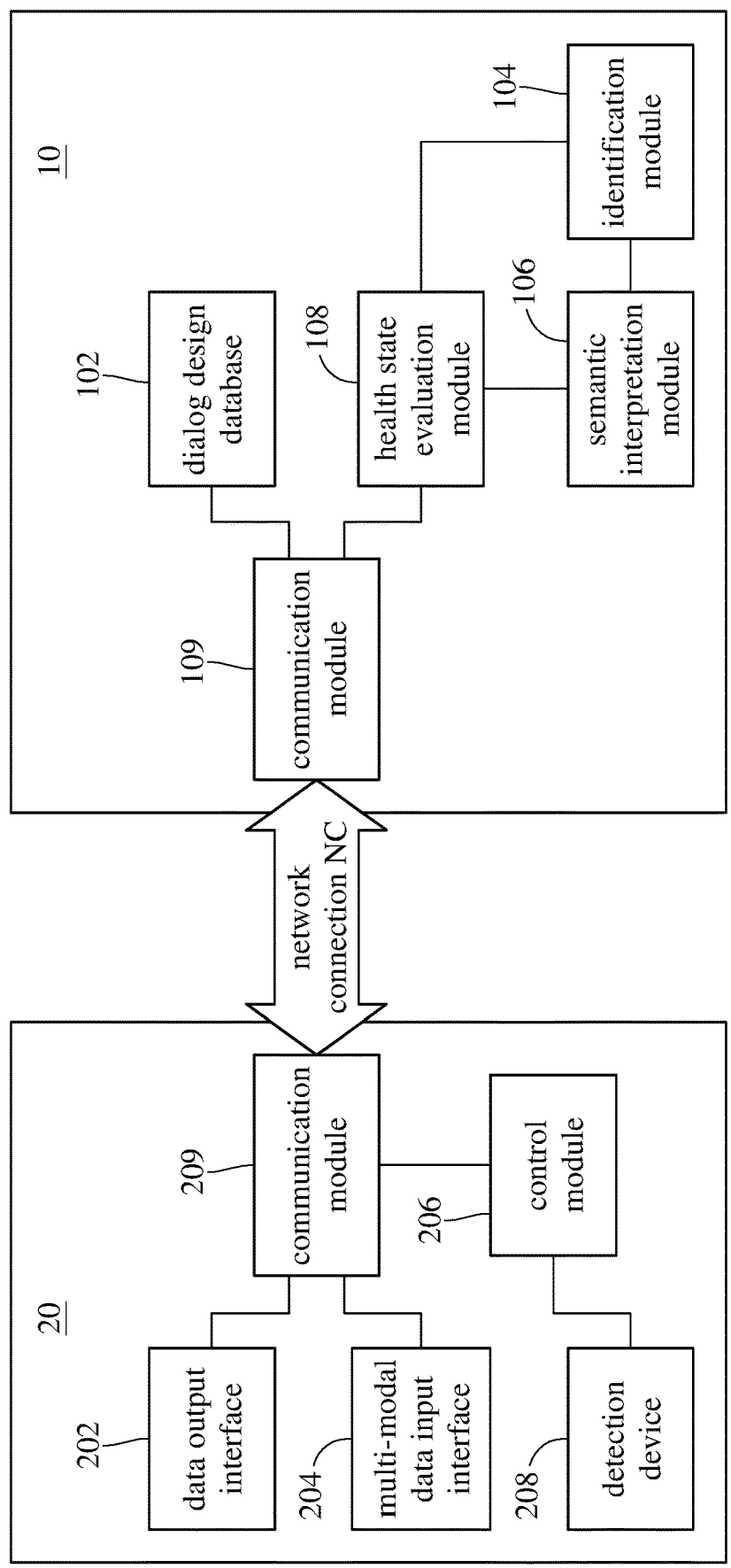
FIG. 1B is a schematic of a block diagram of an interactive health status assessment system according to another embodiment of the present disclosure.

Please refer to FIG. 1B, which is a block diagram of an interactive health status assessment system according to another embodiment of the present disclosure, including an evaluation device 10 and an interaction device 20 that are communicatively coupled to each other, for example, by a wired or wireless network connection NC. However, the present disclosure is not thus limited.

The evaluation device 10 of this embodiment is, for example, a cloud platform, and includes a dialog design database 102, an identification module 104, a semantic interpretation module 106, a health status assessment module 108, and a communication module 109, wherein the functions and configurations of the components 102-108 have been illustrated previously and thus would not be repeated again.

Specifically, the communication module 109 is electrically connected to the dialog design database 102 and the health status assessment module 108. The communication module 109 converts the selected health status assessment question and the evaluation report into a data format (for example, a network packet) for the selected health status assessment question and the evaluation report to be sent to the interactive device 20 through the network connection NC.

In addition, the evaluation device 10 may further include a database such as a living resource, a learning resource, a content resource, or a language database, a user database, and the alike. In the interactive health status assessment system according to an embodiment of the present disclosure, the user database is communicatively connected with the health status assessment module 108, and is used to identify the corresponding user according to the user's facial image or the user's voice, and the evaluation report would also be stored in this user database.

The interactive device 20 is, for example, a mobile vehicle (for example, a robot) or a mobile device (for example, a smart phone or a tablet) that can be equipped with an imaging device, and the interactive health status assessment system is in the form of an application (APP) installed on the interaction device 20. The interaction device 20 includes a data output interface 202, a multimodal data input interface 204, a control module 206, a detection device 208, and a communication module 209. For the function and configuration of components 202~206, please refer to the previous section, and the details are not repeatedly described here. The communication module 209 communicatively couples to the data output interface 202, the multimodal data input interface 204 and the control module 206, and the control module 206 is communicatively coupled to the detection device 208 in this embodiment.

The detection device 208 is, for example, an imaging device or a microphone for obtaining an image data or an audio data, and the obtained data is sent to the control module 206 to determine whether there is a user being detected. Specifically, when the image data contains a user's facial image or the audio data contains the user's voice, the control module 206 selects one health status assessment question from the dialog design data bases 102 via the network connection NC through the communication module 109.

Based on the above two embodiments, it can be understood that while integrating all the components of the interactive health status assessment system into one hardware device, the three embodiments described below are also included.

Embodiment 1

The system is installed in a mobile vehicle with an imaging device, and the system can detect whether the user is around, send a greeting to the user, and activate the system function by a dialogue or command through the imaging device. After the user operates the system function, the system uploads the operation history to the cloud database, and updates the functions of the system-related components. Finally, the system exports the charts and reports to the user, providing the user further learning and reference.

Embodiment 2

The system is installed in the mobile vehicle, and the system can actively engage in dialogue and interaction with the user. Through the process of interacting and establishing of the knowledge base, the system can understand the concepts that the user lacks and provide the user corresponding learning list.

Embodiment 3

The system is installed in the mobile device, and the system can actively engage in dialogue and interaction with the user. Through establishing a database of related information such as the process, time, situation and lifestyle of the dialogue, the system can recommend a personalized list to the user to improve their convenience.

Figure 2:
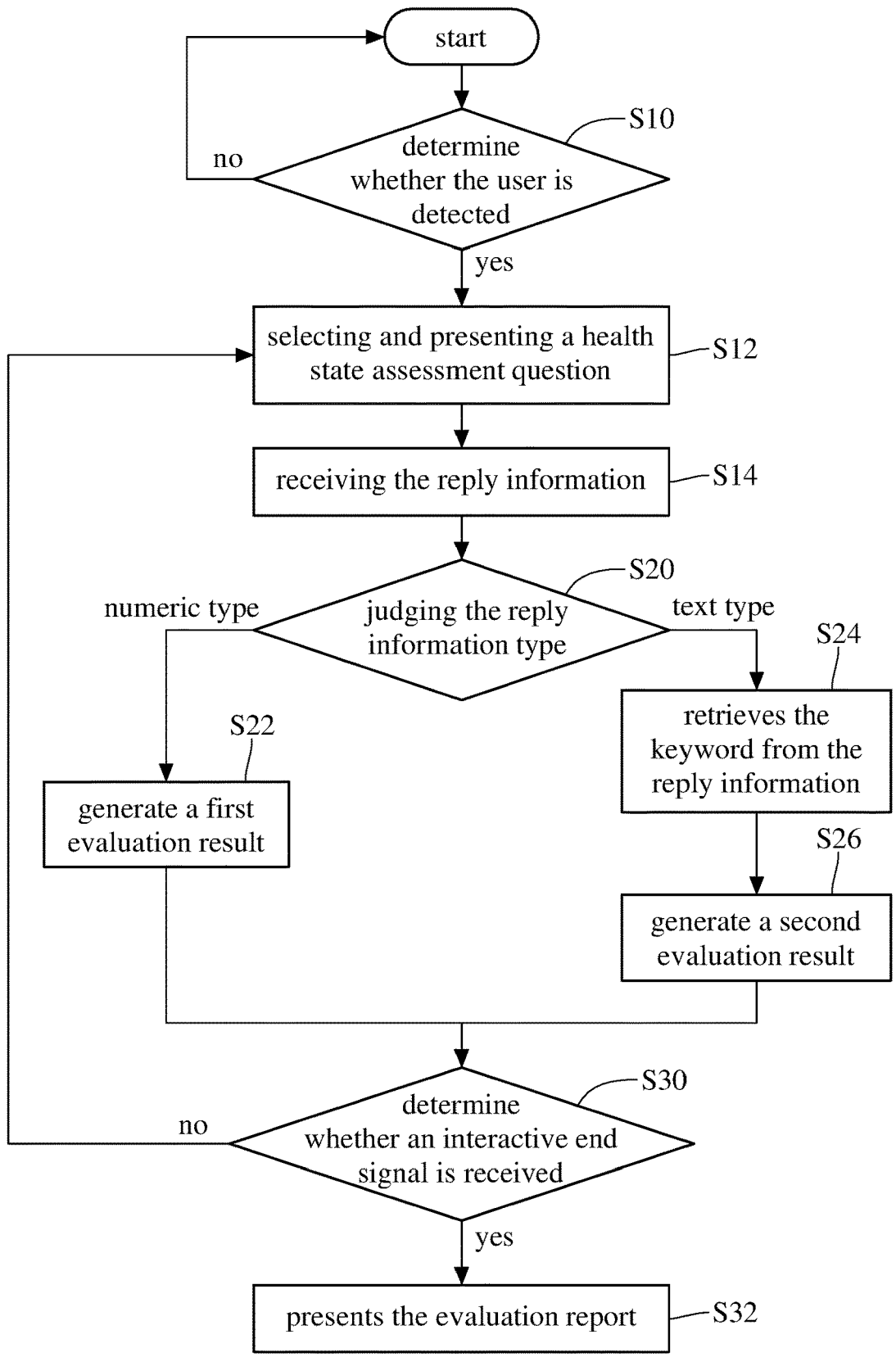
FIG. 2 is a flow chart of an interactive health status assessment method according to an embodiment of the present disclosure.

Please refer to FIG. 2, which is a flowchart of executing of an interactive health status assessment method according to an embodiment of the present disclosure.

Please refer to step S10: determining whether the user is detected. In detail, the detecting device 208 obtains image data or audio data; and the control module 206 determines whether the image data has included the facial image or voice data of the user. When the image data has included the facial image of the user or the audio data has included the voice data of the user, the process goes to step S12, otherwise the detection device 208 continues the detecting process. In addition, the system can detect the user through the detecting device 208 and send a greeting. The user can also directly send a command to the system through the multimodal data input interface 204 to start the system to have a dialogue.

Please refer to step S12: selecting and presenting a health status assessment question. In particular, the system selects a health status assessment question from the dialog database 102 and presents the health status assessment question by the data output interface 202.

Please refer to step S14: receiving the response information. In detail, the system receives the response information of the user's voice, image, or physiological measurement signal through the multimodal data input interface 204. For example, the voice data is received through the sensing module, the trigger signal is received through the touch screen, or the Bluetooth input signal or the wireless input signal is received through the communication module.

Please refer to step S20: determining the response information type. In detail, the system determines whether the response information belongs to a numeric type or a text type by the identification module 104. When the response information belongs to the numerical type, referring to step S22, the health status evaluation module 108 generates a first evaluation result according to the response information and the preset numerical rule. On the other hand, when the response information belongs to the text type, referring to steps S24 to S26, the semantic interpretation module 106 retrieves the keyword from the response information, and then the health status assessment module 108 generates a second evaluation result based on the keyword. The health status assessment module 108 further stores at least one of the above two evaluation results in a temporary storage space.

Please refer to step S30: determining whether an interactive terminating signal is received. In detail, when the interactive terminating signal is not received, another health status assessment question is selected from the follow-up item of the health status assessment question, and the process returns to step S12. Determining whether the interactive terminating signal is received includes the following methods: receiving a trigger signal which represents terminating the interaction; or the follow-up item of the health status assessment question corresponding to zero health status assessment questions.

Conversely, when the system has received the interactive terminating signal, the health status assessment module 108 outputs an evaluation report based on the data in the temporary storage space, and presents the evaluation report through the data output interface 202, as shown in step S32. In addition, before outputting the evaluation report, the method further includes: searching for a storage space of the corresponding user according to the user's facial image or the user's voice; and storing the evaluation report in the storage space corresponding to the current user.

In summary, the interactive health status assessment system and method thereof according to the present disclosure can be introduced into a home robot or an APP, and applied to a family to achieve a companion demand for soothing the pressure of the aging society and long-term care. It can also be applied to the medical caring fields to replace repetitive health education for medical staff, so that medical staff can focus on individual care of patients to improve and optimize the medical quality.

Although the present disclosure has been disclosed above in the foregoing embodiments, it is not intended to limit the invention. Within the scope of the invention, it can modified without departing from the spirit of the invention. Please refer to the attached patent application for the scope of protection defined by the present disclosure.

What is claimed is:

1. An interactive health status assessment method, comprising:
    selecting a health status assessment question from a dialog design database, and presenting the health status assessment question by a data output interface, wherein the dialog design database comprises a plurality of health status assessment questions, and each of the health status assessment questions has a follow-up item corresponding to zero or at least one other health status assessment question in the dialog design database;
    receiving a reply message by a multimodal data input interface after the health status assessment question is presented by the data output interface;
    determining the type of the reply message by an identification procedure;
    generating a first assessment result according to the reply message and a numerical rule by a health status assessment procedure and storing the first assessment result in a temporary storage space when the reply message is of a numerical type;
    extracting a keyword from the reply message by a semantic interpretation procedure and generating a second assessment result according to the reply message by the health status assessment procedure and storing the second assessment result in the temporary storage space when the reply message is of a text type;

determining whether an interaction end signal is received after generating the first assessment result or the second assessment result;
outputting an assessment report according to the data in the temporary storage space by the health status assessment procedure when the interaction end signal has been received; and
selecting another health status assessment question wherein said another health status assessment question is selectively selected from the follow-up item when the interaction end signal has not been received, wherein each of the health status assessment questions has a trigger keyword set, and selecting said another health status assessment question further comprises:
searching in the trigger keyword sets and finding a health status assessment question corresponding to the trigger keyword set from the health status assessment questions to serve as said another health status assessment question,
wherein the follow-up item includes a plurality of candidate questions, after selecting said another health status assessment question, the method further comprises:
determining whether a user completion degree of an intent category to which said another health status assessment question belongs reaches a preset threshold, wherein the user completion degree is a percentage obtained by dividing the number of health status assessment questions that have the corresponding reply messages by the total number of the plurality of health status assessment questions in the intent category;
when the user completion degree does not reach the preset threshold, selecting yet another question from the follow-up item which belongs to the same intent category as the health status assessment question; and
when the user completion degree reaches the preset threshold, selecting yet another health status assessment question of another intent category.

2. The interactive health status assessment method according to claim 1, wherein each of the health status assessment questions has a response keyword set corresponding to the follow-up item, and selecting said another health status assessment questions further comprises:
selecting the follow-up item corresponding to the response keyword set when the keyword meets the response keyword set.

3. The interactive health status assessment method according to claim 1, wherein before selecting the health status assessment question from the dialog design database, the method further comprises:
acquiring an image data or a voice data by a detecting device;
determining whether the image data has a facial image of a user or whether the voice data has a voice signal of the user; and
starting to select the health status assessment question from the dialog design database when the image data has the facial image of the user or the voice data has the voice signal of the user.

4. The interactive health status assessment method according to claim 1, wherein determining whether the interaction end signal is received comprises:
receiving a trigger signal for ending the interaction, or the follow-up item of the health status assessment question corresponding to zero health status assessment question.

5. The interactive health status assessment method described in claim 3, wherein before outputting the assessment report, the method further comprises:
searching for a storage space corresponding to the user according to the facial image of the user or the voice signal of the user from a user database; and
storing the assessment report in the storage space.

6. An interactive health status assessment system, including:
a dialog design database comprising a plurality of health status assessment questions, each of the health status assessment questions having a follow-up item corresponding to zero or at least one other health status assessment question in the dialog design database;
a data output interface, communicatively connected to the dialog design database, and the data output interface is configured to present the health status assessment question;
a multimodal data input interface configured to receive a reply message;
an identification module, connected to the multimodal data input interface, and the identification module is configured to determine that the reply message belongs to a text type or a numerical type;
a semantic interpretation module, communicatively connected to the identification module, and the semantic interpretation module is configured to extract a keyword from the reply message belonging to the text type;
a health status assessment module, communicatively connected to the identification module and the semantic interpretation module, wherein the health status assessment module is configured to generate a first assessment result according to the reply message belonging to the numerical type and a numerical rule, to generate a second assessment result according to the keyword, to store the first and the second assessment results to a temporary storage space ,and to output an assessment report based on the data stored in the temporary storage space; and
a control module, communicatively connected to the dialog design database, the multimodal data input interface and the health status assessment module, the control module is configured to notify the health status assessment module to output the assessment report when receiving an interaction end signal, and selecting another health status assessment question when the interaction end signal is not received, wherein said another health status assessment question is selectively selected from the follow-up item,
wherein each of the health status assessment questions further has a trigger keyword set, and the control module is further configured to use the trigger keyword set in the health status assessment questions to find a health status assessment question corresponding to the trigger keyword set from the health status assessment questions to serve as said another health status assessment question
wherein the follow-up item includes a plurality of candidate questions, after selecting said another health status assessment question, the control module further determines whether a user completion degree of an intent category to which said another health status assessment question belongs reaches a preset threshold, wherein the user completion degree is a percentage obtained by dividing the number of health status assessment questions that have the corresponding reply messages by the total number of the plurality of health status assessment questions in the intent category, the control module selects yet another question from the follow-up item which belongs to the same intent category as the health status assessment question when the user completion degree does not reach the preset threshold, and selects yet another health status assessment question of another intent category when the user completion degree reaches the preset threshold.

7. The interactive health status assessment system of claim 6, wherein each of the health status assessment questions has a response keyword set corresponding to the follow-up item, and the control module is further configured to determine whether the keyword meets the response keyword set, and when the keyword matches the response keyword set, select the follow-up item corresponding to the response keyword set.

8. The interactive health status assessment system as described in claim 6 further includes:

a detecting device, communicatively connected to the control module, and the detecting device is configured to obtain an image data or a voice data, the control module is further connected to the data output interface, and is further configured to determine whether the image data has a user's facial image or whether the voice data has the user's voice, and when the image data has the user's facial image or the voice data has the user's voice, the control module further includes selecting the health status assessment question from the dialog design database and presenting the health status assessment question by using the data output interface.

9. The interactive health status assessment system as described in claim 1 further comprises:

a user database, connected to the health status assessment module for searching for a storage space corresponding to the user based on a facial image of the user or a voice of the user, and storing the assessment report in the storage space.

* * * * *